United States Patent [19]

Bordt et al.

[11] 4,070,453

[45] Jan. 24, 1978

[54] DIPLOID PORCINE EMBRYONIC CELL STRAINS, CULTURES PRODUCED THEREFROM, AND USE OF SAID CULTURES FOR PRODUCTION OF VACCINES

[75] Inventors: Dale Emil Bordt; Phillip Clay Thomas, both of Des Moines, Iowa

[73] Assignee: Syntex (U.S.A.) Inc., Palo Alto, Calif.

[21] Appl. No.: 700,251

[22] Filed: June 25, 1976

[51] Int. Cl.$^2$ .................. A61K 39/12; C12B 3/00; C12K 9/00
[52] U.S. Cl. ........................................... 424/89; 195/1.8
[58] Field of Search ........................... 195/1.8; 424/89

[56] References Cited

U.S. PATENT DOCUMENTS

| | | | |
|---|---|---|---|
| 3,709,782 | 1/1973 | Smith et al. | 195/1.8 |
| 4,003,789 | 1/1977 | Green | 195/1.8 |

*Primary Examiner*—Sam Rosen
*Attorney, Agent, or Firm*—Gerard A. Blaufarb

[57] ABSTRACT

Diploid porcine embryonic cell strains, method of growing same from porcine embryonic tissue, culturing and subculturing said diploid cell strains, and preparing a virus vaccine (exemplary of the virus vaccine thus prepared is a porcine transmissible gastroenteritis virus vaccine) from said diploid cell strain cultures. A novel nutrient growth medium composition for culturing and subculturing by serial subcultivation is also disclosed.

11 Claims, No Drawings

DIPLOID PORCINE EMBRYONIC CELL STRAINS, CULTURES PRODUCED THEREFROM, AND USE OF SAID CULTURES FOR PRODUCTION OF VACCINES

This invention relates to cell strains, particularly to novel diploid porcine embryonic cell strains, methods of growing same from porcine embryonic tissue, culturing and subculturing said diploid cell strains, and preparing a virus vaccine, and particularly a porcine virus vaccine from said diploid porcine embryonic cell strain cultures. Exemplary of a vaccine thus prepared is one from porcine transmissible gastroenteritis virus. This invention also relates to a novel nutrient growth medium composition for culturing and subculturing said diploid porcine embryonic cell strains.

It has been known to grow viruses which cause disease states in many species, such as porcine transmissible gastroenteritis (TGE) virus, bovine virus diarrhea (BVD) virus, infectious canine hepatitis (ICH) virus, rabies (R) virus, and hog cholera (HC) virus, and the like, in primary tissue cultures of porcine origin. However, the use of porcine primary tissue cultures for the growing of viruses suffers from the disadvantage that the porcine primary tissue cultures are prone to contamination with not easily detectable viruses and the probability of which cannot be thoroughly established prior to the actual use of the porcine primary tissue culture in vaccine component preparation. Hence, purity of vaccines prepared using porcine primary tissue cultures is not established until well after the preparation of the vaccine component.

It had been proposed, as a theoretical alternative to the use of porcine primary tissue cultures for vaccine preparation, that cultures, termed continuous porcine cell lines, having the potential of being stored frozen and possessing unlimited growth potential be used. Such continuous cell lines can be established directly from tumors, arise unpredictably spontaneously from cell strains, or result from transformation of cell strains by certain viral or chemical means. Continuous cell lines are usually aneuploid with a subtetraploid karyotype and contain chromosomes displaying structural anomalies. Continuous cell lines do not display contact inhibition, but grow in dense piles of randomly arranged cells that have a "transformed" appearance from that of the normal cell.

However, a cell line while theoretically having an infinite life is undesirable for virus preparation since it has become "transformed", i.e., the chromosome composition has become deviant and carries within it the potential of tumorigenic or oncogenic properties.

It has also been posited (Sanders, Contamination in Tissue Culture, Academic Press, p. 243, 1973) that through subculture cells become susceptible to passenger viruses and lower subculture cells could be considered genetically incapable, or less capable, of reproducing the virus in large amounts until, through more cell subculture, they become susceptible to infection. For example, primary cell cultures established from Burkitt's lymphoma tissue rarely produce Epstein-Barr virus; however, after a number of subcultures of the cells, the virus becomes readily detectable.

Moreover, in obtaining tissue for preparing cell strain cultures, cells from neonatal or mature animals suffer the disadvantage of the donor animal having possibly been exposed directly to infectious agents in the environment and by the birth process. Cells from surgically derived embryos have the advantage of being more effectively protected from exposure to the agents in the environment because of the surrounding uterine and fetal membranes. Thus, for example, removal of the feti from the gravid uterus obtained by hysterectomy shields the tissue source from exposure associated with the birth process.

We have found a novel system for preparing vaccines, based upon the use of surgically derived embryonic diploid porcine origin cell strains demonstrably free of detectable adventitious agents appearing after serial subculturing and without chromosomal anomalies. The system involves the use of cells from surgically obtained embryonic porcine tissues, stored frozen at convenient subculture levels, thoroughly tested for purity and karyotypic normalcy and limited to subculture levels and numbers of cell doublings demonstrably below that level at which cellular transformation occurs.

In addition, our novel diploid porcine embryonic cell strain does not become senescent at the early stages commonly exhibited by primary tissue culture cells.

We have invented a new diploid porcine cell strain comprised of cells derived from surgically obtained porcine embryonic tissue, preferably porcine embryonic kidney, capable of supporting the growth of viruses, e.g., porcine TGE virus (and particularly living, attenuated TGE virus), as well as bovine enteroviruses (BEV), bovine adenoviruses (BAV), porcine parvovirus (PPV), parainfluenza 3 virus ($PI_3$), reovirus (RV), and enteric cytopathic porcine orphan (ECPO) viruses, BVD virus, and rabies (R) virus.

According to the present invention, in the first aspect, there is provided a diploid porcine embryonic cell strain, comprised of cells derived from a surgically obtained porcine embryo which is capable of supporting the growth of viruses.

In the second aspect, there is provided a method for producing a diploid porcine embryonic cell strain in which the appropriate embryonic tissue is disassociated, cultured, and subcultured in a novel nutrient growth medium composition, which facilitates said culturing and subculturing.

A third aspect is the provision of a diploid porcine embryonic cell strain that is capable of being preserved over a long period of time by freezing and which, after thawing and subculturing, retains desirable growth and virus susceptibility characteristics, while at the same time permitting examination for purity, growth potential, virus susceptibility, chromosome composition and tumorigenic properties prior to actual use of the diploid porcine embryonic cell strain for vaccine preparation.

A fourth aspect is a method for growing a vaccine virus, particularly a living, attenuated vaccine virus, wherein a culture of the diploid porcine embryonic cell strain is infected with the vaccine virus and then cultured in an appropriate nutrient medium.

A fifth aspect is the provision of an antigenic material that is obtained from a virus grown on the diploid porcine embryonic cell strain culture and the virus obtained thereby in a form and dosage suitable for adminstration; for example, a living, attenuated strain of TGE virus is propagated in a diploid porcine embryonic cell strain culture and the living attenuated virus so obtained is presented in the form of a vaccine for the immunization of swine against TGE.

It is known that cell strains are cell systems derived from normal tissue, removed from healthy living organisms, that are capable of being subcultured in vitro in a nutrient medium while remaining substantially diploid.

The diploid porcine embryonic cell strains of the present invention provide host cells for growing viruses. These diploid porcine embryonic cell strains are free from specific viral, bacterial, and mycoplasmal contamination and are nontumorigenic as required by 9 CFR 113 (1975); remain diploid and without chromosome anomalies and retain their marker chromosomes, through many population doublings. In addition, they also retain a substantially constant degree of viral susceptibility. This is in contrast to lack of uniformity and potential contaminants that are associated with many primary porcine tissue cultures. In addition, the diploid porcine embryonic cell strains of our invention are capable of being made available in virtually any quantity.

The porcine embryos utilized in preparing the diploid porcine embryonic cell strains of this invention are surgically obtained in random stages of embryonic development from about the third to about the thirteenth week of gestation as determined by fetal measurements [Marable et al, J. Agri. Sci., Camb., Vol. 69:443, (1967)] and/or the breeding records of sows utilized.

Embryos or parts of embryos are removed from the gravid uterus under aseptic conditions and the tissues are disassociated by the use of either mechanical means or use of enzymes, e.g., pancreatic enzymes (such as trypsin), plant enzymes (such as papain), bacterial enzymes (such as pronase and collagenase), and/or chemicals, chelating agents, e.g., ethylenediamine tetraacetic acid (EDTA), and the like, contained in an appropriate solution, or a combination of mechanical and chemical means in any order, e.g., mincing, followed by trypsin and EDTA treatment, or the like, grown in our novel medium described more fully below, and incubated at a temperature of from about 25° C to about 45° C, preferably at from about 35° C to about 39° C and optimally at about 37° C. The cell growth is monitored by microscopic observation and the nutrients may be partially or completely replenished as considered necessary, according to procedures well known in the art.

The novel nutrient growth medium is comprised of salts, carbohydrates, vitamins, lipids (preferably solubilized), proteins, growth factors, cholesterol, and serum. More particularly, based upon the use of one liter of Eagle's Minimum Essential Medium (MEM) containing Earle's salts, a representative nutrient medium is comprised of the following:

| Ingredient | Amount |
| --- | --- |
| L-glutamine | 146 to 584 mg/liter |
| Lactalbumin hydrolysate (LAH) | 2,500 to 10,000 mg/liter |
| NaHCO$_3$ | 213 to 4,400 mg/liter |
| Vitamin E (α-tocopherol acetate) | 0.05 to 0.2 mg/liter |
| Lipid | 2.5 to 10 mg/liter |
| Cholesterol | 0.1 to 0.4 mg/liter |
| Serum | to provide a final concentration of from about 0.1% to about 20% |
| Eagles's MEM containing Earle's salts | q.s. to 1 liter |
| pH (adjusted with acid or base) | 6.0 to 8.0 |

A more preferred nutrient growth medium is one comprising:

| Ingredient | Amount |
| --- | --- |
| L-glutamine | 250 to 350 mg/liter |
| Lactalbumin hydrolysate (LAH) | 4,000 to 6,000 mg/liter |
| NaHCO$_3$ | 300 to 2,500 mg/liter |
| Vitamin E (α-tocopherol acetate) | 0.08 to 0.12 mg/liter |
| Tween 80 (polyoxyethylene sorbitan monooleate) | 3 to 7 mg/liter |
| Cholesterol | 0.15 to 0.3 mg/liter |
| Bovine Serum | to provide a final concentration of from about 5% to about 15% |
| Eagle's MEM containing Earle's salts | q.s. to 1 liter |
| pH (adjusted with hydrochloric acid) | 7.1 to 7.3 |

Suitable solubilized lipid sources are the Tweens® (polysorbates) e.g., Tween® 80 (polyoxyethylene sorbitan monooleate), Tween® 60 (polyoxyethylene sorbitan monostearate), Tween® 40 (polyoxyethylene sorbitan monopalmitate) and the like, with Tween® 80 being preferred.

For the pH adjustment suitable acids are organic and inorganic acids, e.g., hydrochloric, sulfuric, acetic, citric, lactic, carbonic acid, and the like; and suitable bases are inorganic and organic bases, e.g., sodium bicarbonate, sodium hydroxide, potassium hydroxide, calcium hydroxide, tris(hydroxymethyl)aminomethane, and the like.

Suitable serum types are bovine, equine, ovine, caprine, porcine, and the like, with bovine serum being preferred.

In addition, antibiotics, e.g., penicillin, streptomycin, gentamicin, mycostatin, neomycin, polymyxin B, amphotericin B, tetracyclines, and the like can also be included.

When the diploid porcine embryonic strain cells have grown adequately, as determined by microscopic examination, they are subcultured. To accomplish subculturing, the diploid porcine embryonic strain cells are either mechanically separated from the growth surface or exposed to an enzyme, e.g., trypsin, pronase, collagenase, and the like, or a chelating agent, e.g., EDTA, or a mixture of enzymes and chelating agents, the number of viable diploid porcine embryonic cells are preferably counted and subcultured in a suitable number of additional culture containers, at an optimal cell concentration, usually of from about 10,000 to about 100,000 cells per cm$^2$ of growth surface in the novel growth medium described above.

Optionally, when a suitable number of diploid porcine embryonic strain cells is available, as monitored by visual observation and viable cell counting procedures, the cell suspension is adjusted to an optimal concentration (1.0 × 10$^6$ to 1.0 × 10$^7$ cells per ml), in the previously described medium containing a cryopreservative, e.g., dimethyl sulfoxide, or glycerol, separately or in combination, and the like. The mixture thus obtained is then subdivided into convenient aliquots in suitable containers and the temperature gradually lowered to subfreezing temperatures, rendering the frozen diploid porcine embryonic cell strain capable of being stored for extended periods of time in a suitable refrigeration apparatus, at from about −50° C to about −273° C, preferably under liquified atmospheric gases (e.g., liquid nitrogen at about −196° C). As subsequently required the frozen diploid porcine embryonic strain cell suspension is thawed, examined for suitable standards of purity and viability and following subculturing utilized for the preparation of the number of cultures needed for preparation of a particular vaccine.

More particularly, in the practice of this invention, the porcine embryonic tissue, preferably porcine embryonic kidney tissue, is removed from the embryo, preferably at about the eleventh to twelfth week of gestation, finely minced and further disassociated by application of a solution of enzymes and/or chemicals as previously described. The diploid porcine embryonic cells are suspended in the novel nutrient growth medium described above, the suspension is placed into sterile vessels containing an acceptable growth surface and incubated at about 37° C.

Upon attainment of sufficient growth, as determined by visual macroscopic and microscopic observation and viable cell counts, the diploid porcine embryonic strain cells are subcultured, either by mechanical means or by application of enzymes and/or chemicals as previously described, e.g., EDTA, either alone, or in combination with an enzyme, as described above, in buffered saline solution. After detachment from the culture surface the cells are suspended in the above described medium and the concentration of viable diploid porcine embryonic strain cells is determined by means well known to the art and fresh subcultures are prepared. These subcultures are grown to provide a sufficiently large number of cells for cryogenic preservation. At such time as a sufficient number of diploid porcine embryonic strain cells are available, the cells are suspended in the growth medium described above, containing 2% to 20% (preferably 7.5%) of dimethyl sulfoxide and frozen in a suitable refrigeration apparatus. Aliquots of this material are thawed and suspended in the novel nutrient growth medium in suitable vessels and incubated at about 37° C. These subcultures in total, or in part, may be further subcultured in a variety of culture types and frozen at progressively higher subculture levels convenient for use, such as, but not limited to, vaccine production.

Cultures are examined for the presence of undesirable characteristics including adventitious agents, tumorigenic potential, and karyotypic instability. Such procedures are accomplished by methods well known to the art (see 9 CFR 113), including inoculation of media, animals, and other cell culture types with the diploid porcine embryonic strain cells, followed by close inspection of such test elements for undesirable changes. Since tests of purity can be performed while a stock of ancestor diploid porcine embryonic strain cells remains frozen there is provided an advantage in processes requiring cells of demonstrated purity.

It has been observed that the diploid porcine embryonic strain cells multiply readily in the novel nutrient growth medium described above, doubling their own number every two to four days. In view of the fact that the cell concentrations are known before and after each subculture, the cumulative number of cell doublings is readily calculated. It has been established that over 83 such doublings are obtainable through at least 36 subculturings, the porcine embryonic strain cells remaining diploid.

The diploid porcine embryonic strain cells thus obtained are capable of promoting replication of a variety of viruses. Viruses demonstrated as being capable of replicating in these diploid porcine embryonic strain cells include, for example, TGE, PPV, BAV, BEV, PI$_3$, RV, R, ECPO and BVD viruses.

The diploid porcine embryonic strain cell cultures are particularly useful for the preparation of living, attenuated TGE virus and a vaccine thereof of a consistent nature. The frozen diploid porcine embryonic strain cell suspensions are thawed, a culture (or cultures) prepared and subcultured. At an appropriate time, the culture (or cultures) is infected with living, attenuated TGE seed virus. The virus-containing fluids from infected cultures contain progeny virus that is used as a vaccine for immunization procedures.

The following examples illustrate the invention but are not to be construed as limiting the same.

EXAMPLE 1

To ascertain the optimal nutritional requirements of diploid porcine embryonic strain cells in tissue culture systems, a series of experiments was initiated. It was previously observed by us in the culturing of primary neonatal porcine kidney cells that the presence of lactalbumin hydrolysate (LAH) was beneficial in the promotion of cell growth and that LAH was most beneficial when used in combination with Eagle's Minimum Essential Medium (MEM), Eagle, Science, Vol. 130:432, 1959, rather than bacic salt solutions such as Hanks' Balanced Salt Solution (HBSS), Hanks et al, P.S.E.B.M., Vol. 71:196, 1949, or Earle's Balanced Salt Solution (EBSS), Earle, Journal National Cancer Inst., Vol. 4:165, 1943.

It was attempted in similar experiments to propagate porcine cells in media such as Ham F-12 Medium (Ham, Proc. Nat'l. Acad. Sci., U.S., Vol. 53:288, 1965); McCoy 5a Medium (Hsu et al, Jrl. Nat'l. Cancer Inst., Vol. 25:221, 1960); and Leibowitz L-15 Medium (Leibowitz, Jrl. Hyg., Vol. 78:173, 1963). Better porcine cell growth was observed with the MEM supplemented with LAH.

In addition, it is well known in the art that serum is usually added to tissue culture mediums to promote cell growth. To determine the optimal type for the growth of diploid porcine embryonic cells, porcine serum, bovine serum, ovine serum, equine serum, and caprine serum in concentrations ranging from 15% to 0.1% were first compared in the propagation of neonatal porcine cells. In the experiments performed, it was determined that all of the sera were capable of promoting neonatal porcine cell growth and that the quality and purity of the serum was of primary importance in the degree of stimulation of porcine cell growth. However, due to its greater availability, bovine serum was selected as the serum of choice for use in the culture of diploid porcine embryonic strain cells.

An experiment was performed establishing the optimal pH for porcine cell growth at 7.2, with an acceptable pH range of 6.0 to 8.0, with a pH range of 7.1 to 7.3 being preferred. Experiments were also conducted to determine optimal buffer systems comparing: (1) bicarbonate; (2) phosphate; and (3) zwitterion systems. The bicarbonate system was selected as being of greatest benefit.

Experiments were also conducted to determine what effect the addition of other substances beneficial to cell growth in other systems would have upon the growth of diploid porcine embryonic cell strains. Substances evaluated included yeast extract, tryptose phosphate broth, Tweens ® (polysorbates), particularly Tween ® 80 (polyoxyethylene sorbitan monooleate), cholesterol, and Vitamin E (α-tocopherol acetate).

From these evaluations the most preferred nutrient growth medium, described in Example 3 below, was established as being beneficial in the promotion of the growth of diploid porcine embryonic cell strains.

EXAMPLE 2

To determine the optimal conditions for disassociating diploid porcine embryonic cells from tissue, the digestive effects of (a) 0.25% trypsin in HBSS; (b) 0.25% trypsin and 0.1% collagenase in Moscona's Saline, Moscona, Cell Res., Vol. 3:535, 1953; (c) 0.1% trypsin in Puck's Saline A (PSA), Puck, Jrl. Exp. Med., Vol. 106:145 1957; (d) 0.1% protease in PSA; and (e) 0.05% trypsin combined with 0.02% ethylenediamine tetraacetic acid (EDTA) were evaluated. Trypsin in HBSS (a), and trypsin combined with EDTA (e), were determined to be preferred for producing more similar and more acceptable diploid porcine embryonic cell yields.

EXAMPLE 3

The kidneys were removed from a porcine embryo obtained at the eleventh to twelfth week of gestation. The membranes were removed and the kidneys were finely minced in a small amount of HBSS. The minced tissue was freed of blood and other tissue debris by rinsing with HBSS. After the rinsing, the rinsed tissue was combined with 50 ml. of HBSS containing trypsin (1:250) at a concentration of 0.25% that had been prewarmed to 37° C. After 15 minutes of stirring at 37° C, this enzyme solution was decanted and discarded and a fresh 50 ml. aliquot of the warm enzyme added. After 20 minutes of stirring at 37° C this second enzyme mixture was decanted into a centrifuge tube containing 2 ml. of cold bovine serum and packed in ice. Trypsinization (trypsin in HBSS) was repeated, additional cells becoming released into suspension, until only clumps of connective material and debris remained.

The cell suspensions were combined and then centrifuged at 4° C. The packed cells were suspended at a ratio of 1:300 in a sterile cell nutrient growth medium (warmed to 37° C) having the following composition:

| Ingredient | Amount |
|---|---|
| L-glutamine | 292 mg/liter |
| LAH | 5,000 mg/liter |
| NaHCO$_3$ | 700 mg/liter |
| Vitamin E (α-tocopherol acetate) | 0.1 mg/liter |
| Tween 80 (polyoxyethylene sorbitan monooleate) | 5.0 mg/liter |
| Cholesterol | 0.2 mg/liter |
| Bovine serum | to provide a final concentration of 10% |
| Eagle's MEM containing Earle's salts | q.s. to 1 liter |
| pH (adjusted with 1.0 N hydrochloric acid) | 7.3 |

The medium also contained approximately 30 units of penicillin per ml and 30μg of streptomycin per ml. although these materials are not absolutely essential.

The ingredients and amounts of the nutrient growth medium can be varied, within the limits set forth above in the body of the specification.

The diploid porcine embryonic cell suspension (in the above nutrient growth medium) was dispensed into sterile containers and incubated at approximately 37° C. Cell monolayers were formed by the sixth day with an individual 128 cm$^2$ monolayer containing 2.8 × 10$^7$ diploid porcine embryonic cells. These monolayers were treated with a mixture of trypsin (0.25%) and EDTA (0.1%) in a buffered saline solution to suspend the diploid porcine embryonic cells. The cells were placed in the nutrient growth medium containing 7.5% dimethyl sulfoxide and frozen to −196° C.

Subsequent revival of this diploid porcine embryonic cell strain and subcultures were performed with the cells frozen at up to the 40th subculture, it being observed that the diploid porcine embryonic cells of the strain remain substantially epithelial in appearance and phenomena associated with transformation have not occurred through 42 subculturings representing approximately 95 cell population doublings.

Frozen diploid porcine embryonic cell strain at the sixth subcluture [ESK-4; American Type Culture Collection No. CL 184 (ATCC No. CL 184)] were examined for sterility by inoculation with trypticase soy broth and fluid thioglycollate medium (see 9 CFR 113.27). Based upon the absence of observable microbial growth in these media, it was concluded that such frozen diploid porcine embryonic cell stocks were free of bacteria, fungi, and yeasts. The frozen diploid porcine embryonic cell strain at the sixth subculture was examined for mycoplasma contamination by inoculation of an appropriate medium consisting of heart infusion broth, yeast autolysate, proteose peptone No. 3, tetrazolium chloride, penicillin, thallium acetate, inactivated horse serum, nicotinamide adenine dinucleotide, and L-cysteine hydrochloride, and found to be free of such contaminants (see 9 CFR 113.28).

Subculturings of diploid porcine embryonic strain cells were normally performed on a weekly basis, although shorter and longer intervals also can be utilized. The procedure was conducted as described above with fresh cultures being inoculated with a diploid porcine embryonic kidney strain cell suspension containing approximately 5.0 × 10$^4$ cells per ml of the nutrient growth medium and approximately 2.0 × 10$^4$ to 5.0 × 10$^4$ cells per cm$^2$ of available culture area.

Similarly, the lungs of the same fetus were removed and cells cultured therefrom.

Likewise, the cells from testicles, kidneys, and lungs from other feti as well as decapitated and eviscerated whole porcine embryos, in approximately the fourth to twelfth weeks of gestation, were cultured.

EXAMPLE 4

Frozen aliquots of the diploid porcine embryonic cell strain (obtained in Example 3) were thawed and planted in culture vessels containing the novel growth medium of Example 3. When they attained confluency (as shown by microscopic examination), they were treated with trypsin and EDTA and subcultured as previously described. Such culture methods were continued until confluent monolayers of the diploid porcine embryonic strain cells were obtained at a desirable subculture level, ten subcultures representing about 23 cell doublings.

The diploid porcine embryonic strain cells were then exposed to an appropriate suspension of living, attenuated TGE virus and the infected cultures were incubated at approximately 37° C, it being observed that the virus infection caused changes to occur in the appearance of the diploid porcine embryonic strain cells. About 24 hours after infection, small grainy areas were noticed which gradually progressed until the majority of the diploid porcine embryonic strain cells were so affected. At convenient intervals the virus-laden fluids were harvested and the cultures replenished with fresh nutrient medium (containing 5% bovine serum). The harvesting-replenishment procedure was carried out until the cultures were spent. The materials thus harvested and found to possess sufficient virus were utilized in the preparation of a vaccine for administration to swine according to the procedure set forth in Example 8 below.

The above procedure was carried out in culture vessels of both the stationary and non-stationary variety, virus fluids of acceptable quality being obtained from either system.

EXAMPLE 5

Following the standard test procedures described in 9 CFR 113, bottle cultures of the diploid porcine embryonic cell strain obtained in Example 3 were subcultured ten times, representing about 23 population doublings. These cultures were incubated at about 37° C for a period of 22 days at which time they were subcultured to the eleventh passage level representing about 25 cell population doublings and maintained an additional six days. The cell monolayers were periodically examined for cytopathogenesis, indicative of infection. Representative cultures were then exposed to 0.2% suspensions of chicken, guinea pig, and human type "O" erythrocytes in phosphate buffered saline and others were stained with hematoxylin and eosin. No evidence of cytopathogenesis, hemadsorption or abnormal cellular inclusions were microscopically observed in the diploid porcine embryonic strain cells.

Still other eleventh passage diploid porcine embryonic strain cells were disrupted by freezing and thawing three times and the resulting fluids then used to inoculate monolayers of primary swine kidney cells, secondary bovine kidney cells, primary canine kidney cells, Vero established cell line, and BHK-21 established cell line. These cultures were incubated at about 37° C for 14 days following inoculation and were then examined microscopically for observable cytopathology and no cytopathology was observed. After observation, the cell cultures were assayed for hemadsorptive agents as described in the preceding paragraph and found free of such contaminants.

Yet other eleventh passage diploid porcine embryonic strain cells were subcultured into Leighton tubes containing coverslips. After appropriate incubation, these coverslips were assayed by the direct fluorescent antibody technique, using specific fluorochrome labeled antibodies, against: $PI_3$ virus, infectious bovine rhinotracheitis (IBR) virus, BVD virus, BEV virus (four serotypes), BAV virus (two serotypes), bovine parvovirus (BPV), R virus, PPV virus, pseudorabies virus (PSV), HC virus, RV virus, porcine adenovirus (PAV) virus, and TGE virus. Examination of the coverslips infected with specific agents as positive test controls indicated the diploid porcine embryonic cell strain was capable, as established by positive fluorescence, of supporting the growth of the following viruses: TGE, PPV, $PI_3$, R, RV, BEV, BAV and BPV.

EXAMPLE 6

Cultures of the diploid porcine embryonic cell strain were subcultured 10 times, representing about 23 cell population doublings, and 36 times representing about 83 cell population doublings. Cells from these cultures that were in mitotic metaphase were examined for karyotypic characteristics (see, for example, Moorhead, Chromosome Cytology and Karyotyping, Diploid Cell Culture Course, Continuing Education Program, W. Alton Jones Cell Science Center, Lake Placid, New York, August 12-16, 1974). The cells were conclusively determined as being diploid in chromosome number and free from detectable chromosomal anomalies and marker chromosomes were present at both levels.

The chromosome numbers contained in these cells were as shown in Table 1.

TABLE I

Chromosome Distribution in Diploid Porcine Embryonic Cell Strain at Subcultures 10 and 36

| Subculture Number | No. Chromosomes/ No. Cells Observed | | | | | | | | Total |
|---|---|---|---|---|---|---|---|---|---|
| | 35 | 36 | 37 | 38 | 39 | 42 | 75 | 76 | |
| 10 | 1 | 4 | 6 | 37 | 1 | 1 | 1 | 1 | 52 |
| 36 | 0 | 0 | 3 | 64 | 0 | 0 | 0 | 1 | 68 |

The normal diploid chromosome complement for Sus scrofa, the domestic pig, has been shown to be 38 (Hsu et al, An Atlas of Mammalian Chromosomes, Springer-Verlag, New York, 1967). Accordingly, the embryonic diploid porcine cell strain that is the subject of this invention, was shown to be and to remain of diploid chromosome complement over a span of 36 subculturings and about 83 population doublings.

EXAMPLE 7

Cultures of the diploid porcine embryonic cell strain were subcultured 10 times, representing about 23 cell population doublings and were then dispersed with a mixture of trypsin (0.25%) and EDTA (0.1%) as described above. These diploid porcine embryonic strain cells ($1 \times 10^5$ viable) were inoculated into the cheekpouches of hamsters that were immunologically depressed by administration of cortisone acetate. Similarly, cortisone acetate immunologically depressed hamsters were inoculated with $1 \times 10^4$ viable BHK-21 cells, known to be tumorigenic. The animals were observed for a period of 60 days after inoculation. No tumors were observed to develop in any animal inoculated with either the diploid porcine embryonic strain cells or a saline solution; all of the hamsters that received BHK-21 cells displayed progressive tumors by the twenty-first post-inoculation day.

EXAMPLE 8

Selected harvests of the TGE virus fluid prepared as described in Example 4 were combined with a virus stabilizer solution containing peptone, salts, sugar, gelatin, and lactalbumin hydrolysate to prepare a vaccine. The final vaccine mixture contained approximately seven parts of virus fluid combined with approximately three parts of virus stabilizer. The virus fluid-virus stabilizer mixture was dispensed in small aliquots in sterile vaccine vials and was then frozen and lyophilized in a freeze-drying apparatus.

Following the lyophilization process, the vials were sealed and the vaccine was storaged in refrigeration at approximately 4° C. Vials of this lyophilized vaccine were randomly selected and assayed for TGE virus titer, bacterial sterility, mycoplasma, and post-lyophilization moisture content (see 9 CFR 113.29). The reconstituted vaccine was found to possess a 50% endpoint viral infectivity titer of $10^{5.94}$ tissue culture infectious doses per 1.0 ml of reconstituted vaccine. The vaccine was shown to be free of bacterial and mycoplasma contamination by the procedures described in Example 3

(see also 9 CFR 113.27 and 9 CFR 113.28). The desiccated vaccine was shown to have a post-lyophilization moisture content of 2.69%.

We claim:

1. A nutrient growth medium for culturing and subculturing a diploid porcine embryonic cell strain which comprises:

| L-glutamine | 146 to 584 mg/liter |
| Lactalbumin hydrolysate | 2,500 to 10,000 mg/liter |
| NaHCO$_3$ | 213 to 4,400 mg/liter |
| Vitamin E (α-tocopherol acetate) | 0.05 to 0.2 mg/liter |
| Polysorbate (Solubilized lipid source) | 2.5 to 10 mg/liter |
| Cholesterol | 0.1 to 0.4 mg/liter |
| Bovine, Equine, Ovine, Caprine or Porcine Serum | to provide a final concentration of from about 0.1% to about 20% |
| Eagle's Minimum Essential Medium containing Earle's Salts | q.s. to 1 liter |
| pH (adjusted with acid or base) | 6.0 to 8.0 |

2. A nutrient growth medium according to claim 1 wherein the following amounts of ingredients are present:

| L-glutamine | 250 to 350 | mg/liter |
| Lactalbumin hydrolysate | 4,000 to 6,000 | mg/liter |
| NaHCO$_3$ | 300 to 2,500 | mg/liter |
| Vitamin E (α-tocopherol acetate) | 0.08 to 0.12 | mg/liter |
| Tween 80 (polyoxyethylene sorbitan monooleate) | 3 to 7 | mg/liter |
| Cholesterol | 0.15 to 0.3 | mg/liter |
| Bovine serum | to provide a final concentration of from about 5% to about 15% | |
| Eagle's Minimum Essential Medium containing Earle's Salts | q.s. to | 1 liter |
| pH (adjusted with hydrochloric acid) | | 7.1 to 7.3 |

3. A diploid porcine embryonic cell strain characterized by:
   A. freedom from
      i. specified viral contaminants as measured by cytopathology, hemadsorption, inclusion body staining, and fluorescent antibody techniques,
      ii. specified bacterial contaminants as measured by sterility testing,
      iii. mycoplasma contamination as measured by brothagar subculturing;
   B. nontumorigenicity in immunologically depressed hamsters;
   C. possessing a substantially constant degree of viral susceptibility;
   D. capable of maintaining substantial diploidy and not becoming senescent after at least 36 subculturings, while remaining free from morphological transformation and chromosomal anomalies; and
   E. retention of marker chromosomes; and a suitable culture medium therefor.

4. The diploid porcine embryonic cell strain of claim 3 which has been subcultured six times with eleven cell doublings and having American Type Culture Collection Accession No. CL 184 (ATCC No. CL 184).

5. A diploid porcine embryonic cell strain of claim 3 capable of being infected by and supportive of the growth of viruses selected from the group consisting of:

| transmissible gastroenteritis | (TGE) virus, |
| porcine parvovirus | (PPV) virus, |
| parainfluenza$_3$ | (PI$_3$) virus, |
| rabies | (R) virus, |
| enteric cytopathic porcine orphan | (ECPO) virus, |
| bovine virus diarrhea | (BVD) virus, |
| reovirus | (RV) virus, |
| bovine enterovirus | (BEV) virus, |
| bovine adenovirus | (BAV) virus, and |
| bovine parvovirus | (BPV) virus. |

6. A diploid porcine embryonic cell strain of claim 4 capable of being infected by and supportive of the growth of a living, attenuated TGE virus.

7. Process for the preparation of a diploid porcine embryonic cell strain characterized by:
   A. freedom from
      i. specified viral contaminants as measured by cytopathology, hemadsorption, inclusion body staining, and fluorescent antibody techniques,
      ii. specified bacterial contaminants as measured by sterility testing,
      iii. mycoplasma contamination as measured by brothagar subculturing;
   B. nontumorigenicity by inoculation of immunologically depressed hamsters;
   C. possessing a substantially constant degree of viral susceptibility;
   D. capable of maintaining substantial diploidy and not becoming senescent after at least 36 subculturings, while remaining free from morphological transformation and chromosomal anomalies; and
   E. retention of marker chromosomes, which comprises;
      1. disassociating the cells from a porcine embryo;
      2. culturing the said disassociated cells in a nutrient growth medium comprising:

| L-glutamine | 146 to 584 | mg/liter |
| Lactalbumin hydrolysate Serial No. 700,251 | 2,500 to 10,000 | mg/liter |
| NaHCO$_3$ | 213 to 4,400 | mg/liter |
| Vitamine E (α-tocopherol acetate) | 0.05 to 0.2 | mg/liter |
| Polysorbate (Solubilized lipid source) | 2.5 to 10 | mg/liter |
| Cholesterol | 0.1 to 0.4 | mg/liter |
| Bovine, Equine, Ovine, Caprine or Porcine Serum | to provide a final concentration of from about 0.1% to about 20% | |
| Eagle's Minimum Essential Medium containing Earle's Salts | q.s. to | 1 liter |
| pH (adjusted with acid or base) | | 6.0 to 8.0 |

3. removing the cultured diploid porcine embryonic strain cells from the nutrient medium by mechanical means, or by exposure to an enzyme, or by exposure to a chelating agent, or by exposure to a mixture of enzymes and chelating agents; and
   4. serially subculturing according to step (2) followed by removal of the cultured diploid porcine embryonic strain cells according to step (3), said serial subcultures and removals being carried out at least 42 times.

8. The process according to claim 7 wherein in step (2) the nutrient growth medium comprises:

| L-glutamine | 250 to 350 | mg/liter |
| Lactalbumin hydrolysate | 4,000 to 6,000 | mg/liter |
| NaHCO$_3$ | 300 to 2,500 | mg/liter |

-continued

| | | |
|---|---|---|
| Vitamin E (α-tocopherol acetate) | 0.08 to 0.12 | mg/liter |
| Tween 80 (polyoxyethylene sorbitan monooleate) | 3 to 7 | mg/liter |
| Cholesterol | 0.15 to 0.3 | mg/liter |
| Bovine serum | to provide a final concentration of from about 5% to about 15% | |
| Eagle's Minimum Essential Medium containing Earle's Salts | q.s. to | 1 liter |
| pH (adjusted with hydrochloric acid) | | 7.1 to 7.3 | and in step (3) the means used for removal of the cultured diploid porcine embryonic strain cells are mechanical or with an enzyme in conjunction with a chelating agent and the said serial subcultures and removals are carried out at least 42 times.

9. The process of claim 7 wherein a virus selected from the group consisting of:

| | | |
|---|---|---|
| transmissible gastroenteritis | (TGE) | virus, |
| porcine parvovirus | (PPV) | virus, |
| parainfluenza$_3$ | (PI$_3$) | virus, |
| rabies | (R) | virus, |
| enteric cytopathic porcine orphan | (ECPO) | virus, |
| bovine virus diarrhea | (BVD) | virus, |
| reovirus | (RV) | virus, |
| bovine enterovirus | (BEV) | virus, |
| Bovine adenovirus | (BAV) | virus, and |
| bovine parvovirus | (BPV) | virus. | is grown on the diploid porcine embryonic strain cells thus produced and a vaccine is produced therefrom.

10. The process of claim 8 wherein a living, attenuated TGE virus is grown on the diploid porcine embryonic cell strain ATCC No. CL 184 thus produced and a vaccine is produced therefrom.

11. A diploid porcine embryonic cell strain having ATCC No. CL. 184 in a suitable culture medium therefor.

* * * * *